US008831723B2

(12) United States Patent
Brown et al.

(10) Patent No.: US 8,831,723 B2
(45) Date of Patent: Sep. 9, 2014

(54) PACE DISCRIMINATION OF TACHYCARDIA USING ATRIAL-VENTRICULAR PACING

(75) Inventors: Mark L. Brown, North Oaks, MN (US); Troy Edward Jackson, New Brighton, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 394 days.

(21) Appl. No.: 12/570,651

(22) Filed: Sep. 30, 2009

(65) Prior Publication Data

US 2011/0077704 A1   Mar. 31, 2011

(51) Int. Cl.
*A61N 1/368*   (2006.01)

(52) U.S. Cl.
USPC ........ 607/14; 607/9; 607/11; 607/15; 607/17; 607/25; 607/26; 607/28; 607/115; 607/116; 607/119; 607/122; 607/123

(58) Field of Classification Search
USPC ........... 607/1–2, 9, 11, 14–15, 17, 25–26, 28, 607/115, 116, 119, 122–123
See application file for complete search history.

(56) References Cited

U.S. PATENT DOCUMENTS

| 5,117,824 A | 6/1992 | Keimel et al. |
| 5,184,615 A | 2/1993 | Nappholz et al. |
| 5,193,550 A | 3/1993 | Duffin |
| 5,354,316 A | 10/1994 | Keimel |
| 5,411,530 A | 5/1995 | Akhtar |
| 5,545,186 A | 8/1996 | Olson et al. |
| 5,893,882 A | 4/1999 | Peterson et al. |
| 6,091,988 A | 7/2000 | Warman et al. |
| 6,393,316 B1 | 5/2002 | Gillberg |
| 7,206,633 B2 | 4/2007 | Saba |
| 7,317,942 B2 * | 1/2008 | Brown ............................ 607/14 |
| 2003/0191404 A1 | 10/2003 | Klein |
| 2004/0088013 A1 | 5/2004 | Stadler et al. |
| 2004/0158292 A1 | 8/2004 | Sheldon et al. |
| 2004/0172067 A1 | 9/2004 | Saba |
| 2004/0220624 A1 | 11/2004 | Ritscher et al. |
| 2006/0217769 A1 | 9/2006 | Saba |
| 2008/0154322 A1 | 6/2008 | Jackson et al. |
| 2008/0269819 A1 | 10/2008 | Zhou |
| 2009/0143832 A1 | 6/2009 | Saba |

OTHER PUBLICATIONS (PCT/US10/049456) PCT Notification of Transmittal of the International Search Report and the Written Opinion of the International Searching Authority.
Daryl P. Ridley, Atrial Response to Ventricular Antitachycardia Pacing Discriminates Mechanism of 1:1 Atrioventricular Tachycardia, J cardiovasc Electrophysiol, vol. 16, pp. 601-605, Jun. 2005.
Samir Saba, Simultaneous Atrial and Ventricul Anti-Tachycardia Pacing as a novel Method of Rhythm Discrimination, J cardiovasc Electrophysiol, vol. 17, pp. 695-701, Jul. 2006.

* cited by examiner

*Primary Examiner* — Deborah Malamud
(74) *Attorney, Agent, or Firm* — Michael C. Soldner

(57) ABSTRACT

A cardiac medical device and associated method control delivery of dual chamber burst pacing pulses in response to detecting tachycardia. A number of cardiac cycles occurring in a first cardiac chamber are identified subsequent to the dual chamber pacing pulses. The number of sensed intrinsic events occurring in a second cardiac chamber during the first chamber cardiac cycles is determined as a number of second chamber events. The tachycardia episode is classified in response to the number of second chamber events.

8 Claims, 10 Drawing Sheets

PACE DISCRIMINATION OF TACHYCARDIA USING ATRIAL-VENTRICULAR PACING

CROSS-REFERENCE TO RELATED APPLICATION

Cross-reference is hereby made to the commonly-assigned related U.S. Applications: U.S. Publication No. 2011/0077705 A1, entitled "PACE DISCRIMINATION OF TACHYCARDIA USING ATRIAL-VENTRICULAR PACING", to Brown et al., and U.S. Publication No. 2011/0077703 A1, entitled "PACE DISCRIMINATION OF TACHYCARDIA USING ATRIAL-VENTRICULAR PACING", to Brown et al., both filed concurrently herewith and incorporated herein by reference in their entireties.

TECHNICAL FIELD

The present disclosure relates generally to cardiac medical devices and to a device and method for monitoring the heart rhythm and delivering atrial-ventricular pacing to the patient for use in discriminating heart rhythms.

BACKGROUND

A typical implantable cardioverter defibrillator (ICD) has the capability of providing a variety of anti-tachycardia pacing (ATP) regimens. Normally, these regimens are applied according to a pre-programmed sequence, and each regimen includes a predetermined number of pacing pulses. After the series of pacing pulses is delivered, the device checks to determine whether the series of pulses was effective in terminating the detected tachycardia. Typically, termination is confirmed by a return to either a demand-paced rhythm or a sinus rhythm in which successive spontaneous depolarizations are separated by at least a defined interval. If the tachycardia is not terminated, the ICD device may deliver a subsequent series of pacing pulses having modified pulse parameters, e.g. reduced inter-pulse intervals and/or an altered number of pulses. When ATP attempts fail to terminate the tachycardia, high-voltage cardioversion shocks may be delivered. Since shocks can be painful to the patient and consume relatively greater battery charge than pacing pulses, it is desirable to avoid the need to deliver shocks by successfully terminating the tachycardia using less aggressive pacing therapies.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length (P-P intervals and R-R intervals respectively) when an SVT is conducted to the ventricles or when a VT is conducted retrograde to the atria. Accordingly, methods are needed for accurately classifying a detected tachycardia as VT or SVT to allow the most appropriate therapy to be delivered by the ICD, with the highest likelihood of success and without unacceptably delaying attempts at terminating the tachycardia.

DETAILED DESCRIPTION

Figure 1:
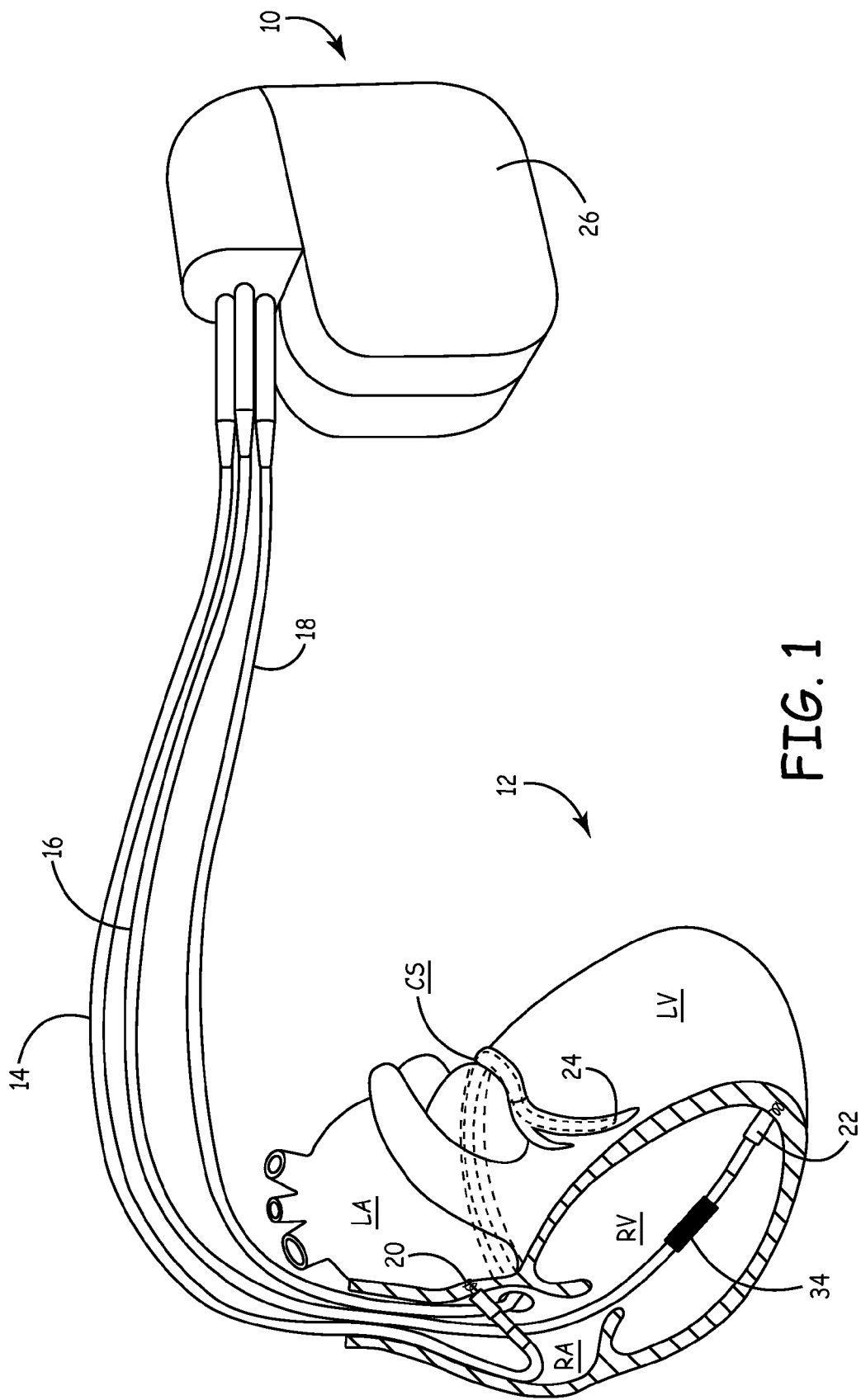
FIG. 1 is a schematic representation of a cardiac medical device.

In the following description, references are made to illustrative embodiments. It is understood that other embodiments may be utilized without departing from the scope of the invention. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic representation of a cardiac medical device 10. Cardiac medical device 10 is embodied as an ICD in FIG. 1, however, methods described herein should not be interpreted as being limited to any particular implantable medical device or any particular cardiac medical device. Instead, embodiments may include any cardiac medical device so long as the device utilizes a plurality of electrodes or other sensors for monitoring the cardiac rhythm of a patient and for delivering pacing pulses to the patient. The electrodes are capable of sensing cardiac EGM or ECG signals, referred to herein collectively as "cardiac signals" in the upper atrial chambers and in the lower ventricular chambers.

In FIG. 1, heart 12 includes the right atrium (RA), left atrium (LA), right ventricle (RV), left ventricle (LV), and the coronary sinus (CS) extending from the opening in the right atrium to form the great cardiac vein. FIG. 1 depicts device 10 in relation to the heart 12. As shown, three transvenous leads 14, 16, and 18 connect the device 10 with the RA, the RV and the LV, respectively. Each lead includes at least one electrical conductor and pace/sense electrode. For example, leads 14, 16 and 18 are respectively connected to pace/sense electrodes 20, 22, and 24. In addition, a can electrode 26 can be formed as part of the outer surface of the housing of the device 10. The pace/sense electrodes 20, 22, and 24 and can electrode 26 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pace pulses.

A coil electrode 34 is also shown as being coupled to a portion of RV lead 16. Coil electrodes can additionally or alternatively be coupled to portions of any of the leads of FIG. 1. The coil electrode 34, or other similar electrode types, can be electrically coupled to high voltage circuitry for delivering high voltage cardioversion/defibrillation shock pulses. Electrodes shown in FIG. 1 can be disposed in a variety of locations in, around, and on the heart.

The leads and electrodes described above can be employed to record cardiac signals in the atria and the ventricles. The recorded data can be periodically transmitted to a programmer or other external device enabled for telemetric communication with the medical device 10.

Figure 2:
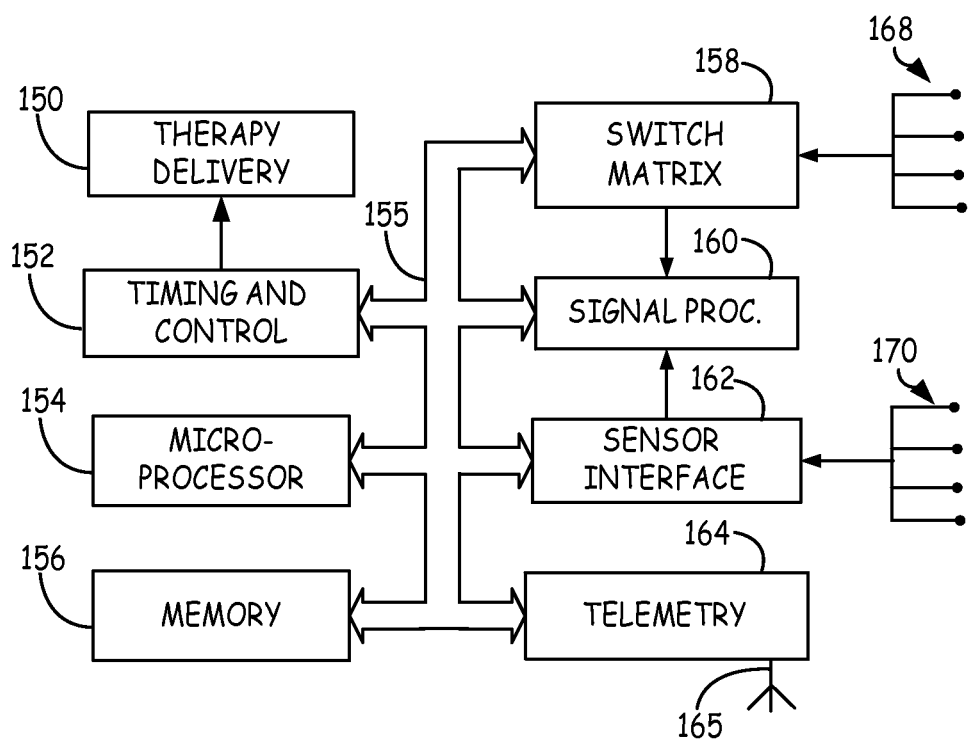
FIG. 2 is a functional block diagram of the cardiac medical device shown in FIG. 1 according to one embodiment.

FIG. 2 is a functional block diagram of the implantable cardiac medical device 10 shown in FIG. 1 according to one embodiment. Cardiac medical device 10, referred to hereafter as ICD 10, generally includes timing and control circuitry 152 and a controller that may be embodied as a microprocessor 154 or a digital state machine for timing sensing and therapy delivery functions in accordance with a programmed operating mode. Microprocessor 154 and associated memory 156 are coupled to the various components of ICD 10 via a data/address bus 155. ICD 10 includes therapy delivery module 150 for delivering electrical stimulation pulses to a patient's heart including cardiac pacing pulses, arrhythmia pacing therapies such as anti-tachycardia pacing (ATP) and cardioversion/defibrillation shocks, under the control of timing and control 152 and microprocessor 154. Therapy delivery module 150 is typically coupled to two or more electrodes 168 via an optional switch matrix 158. Electrodes 168 may include the electrodes shown in FIG. 1. Switch matrix 158 is used for selecting which electrodes and corresponding polarities are used for delivering electrical stimulation pulses.

Cardiac electrical signals are sensed for determining when an electrical stimulation therapy is needed and in controlling a stimulation mode and the timing of stimulation pulses. Electrodes used for sensing and electrodes used for stimulation may be selected via switch matrix 158. When used for sensing, cardiac signals received by electrodes 168 are coupled to signal processing circuitry 160 via switch matrix 158. Signal processor 160 includes sense amplifiers and may include other signal conditioning circuitry such as filters and an analog-to-digital converter. Cardiac electrical signals may then be used by microprocessor 154 for detecting physiological events, such as detecting and discriminating cardiac arrhythmias. Signal processing circuitry 160 may include event detection circuitry generally corresponding to P-wave or R-wave detection circuitry as disclosed in U.S. Pat. No. 5,117,824 (Keimel, et al.), hereby incorporated herein by reference in its entirety.

Arrhythmia detection algorithms may be implemented for detecting ventricular tachycardia (VT), ventricular fibrillation (VF) as well as atrial arrhythmias such as atrial fibrillation (A FIB). Sensed ventricular event intervals (R-R intervals) and sensed atrial event intervals (P-P intervals) measured from the sensed cardiac signals are commonly used for detecting and discriminating atrial and ventricular arrhythmias. Additional information obtained such as R-wave morphology, slew rate, other event intervals (e.g., P-R intervals) or other sensor signal information may be used in detecting, confirming or discriminating an arrhythmia. Reference is made, for example, to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals and the provision of arrhythmia therapies in response to arrhythmia detection and discrimination, all of which patents are incorporated herein by reference in their entirety.

In one detection scheme, programmable detection interval ranges designate the range of sensed event intervals indicative of a tachycardia and may be defined separately for detecting slow tachycardia, fast tachycardia and fibrillation. In addition to event interval information, the morphology of the EGM signal may be used in discriminating heart rhythms. As will be described herein, the cardiac signal response to dual chamber burst pacing delivered in response to detecting both atrial and ventricular tachycardias can be used to discriminate between SVT and VT. Microprocessor 154 may initiate atrial-ventricular pacing, referred to herein as dual chamber pacing, for use in tachycardia discrimination particularly when the sensed atrial and ventricular rates are so similar that other tachycardia detection methods are not sensitive enough to discriminate between VT and SVT.

In response to arrhythmia detection, a programmed arrhythmia therapy is delivered by therapy delivery module 150 under the control of timing and control 152. Arrhythmia therapies may include tiered therapies in which less aggressive ATP regimens are delivered first and, when not successful, a high voltage shock therapy is delivered. A description of high-voltage output circuitry and control of high-voltage shock pulse delivery is provided in the above-incorporated '186 Olson patent.

ICD 10 may additionally be coupled to one or more physiological sensors 170 carried by leads extending from ICD 10 or incorporated in or on the ICD housing. Signals from sensors 170 are received by a sensor interface 162 which provides sensor signals to signal processing circuitry 160. Sensor signals may be used by microprocessor 154 for detecting physiological events or conditions.

The operating system includes associated memory 156 for storing a variety of programmed parameter values that are used by microprocessor 154. The memory 156 may also be used for storing data compiled from sensed physiological signals and/or relating to device operating history for telemetry out on receipt of a retrieval or interrogation instruction. Parameters and tachycardia discrimination rules and algorithms may be stored in memory 156 and utilized by microprocessor 154 for controlling the delivery of dual chamber pacing and discrimination of detected tachycardia episodes based on the cardiac response to the dual chamber pacing. In one embodiment, memory 156 stores a set of tachycardia discrimination rules relating to a heart's response to dual chamber burst pacing.

A burst of pacing pulses, i.e. a programmed number of pacing pulses delivered at a rate faster than a detected tachycardia in both the atria and the ventricles, is used for tachycardia discrimination. The pacing burst is not necessarily intended to terminate the tachycardia, unlike programmed ATP regimes. In some cases, however, it is possible that the burst of pacing pulses does terminate the tachycardia. The burst of pacing pulses are delivered at a fixed pacing pulse interval in the illustrative embodiments described herein, however it is conceivable that dual chamber pacing pulses delivered for tachycardia discrimination may be delivered at a progressively shortened interval, commonly referred to as "ramp" pacing, or any combination of fixed rate burst pacing pulses and ramp pacing pulses.

As will be described in greater detail herein, in response to detecting a tachycardia, microprocessor 154 will cause timing and control 152 to enable therapy delivery module 150 to deliver a burst of pacing pulses in both the atria and the ventricles. Tachycardia discrimination rules relating to the heart's response to the dual chamber burst pacing will be selected and applied by microprocessor 154 for discriminating the detected tachycardia as SVT or VT.

ICD 10 further includes telemetry circuitry 164 and antenna 165. Programming commands or data are transmitted during uplink or downlink telemetry between ICD telemetry circuitry 164 and external telemetry circuitry included in a programmer or monitoring unit.

A recent technique to distinguish VT from SVT using dual chamber pacing delivery is generally described in U.S. Pat. No. 7,206,633 (Saba). Briefly, simultaneous pacing is delivered in the atria and in the ventricle (dual chamber pacing) after detecting tachycardia. The earliest arriving electrical signal sensed following the dual chamber pacing is used to diagnose the detected tachycardia as SVT or VT. It is assumed that the chamber in which the fast rhythm is originating will be identifiable by the earliest occurring intrinsic event subsequent to dual chamber pacing. If the earliest intrinsic signal is sensed in the atrium after stopping the simultaneous dual chamber pacing, the detected tachycardia is classified as SVT. If the earliest intrinsic signal is sensed in the ventricle, the detected tachycardia is classified as VT.

While this particular simultaneous pacing technique can be used to effectively differentiate between arrhythmias originating in the ventricular and supraventricular regions of the heart in many cases, this technique has been found by the inventors to, at times, lead to false detections.

Figure 3:
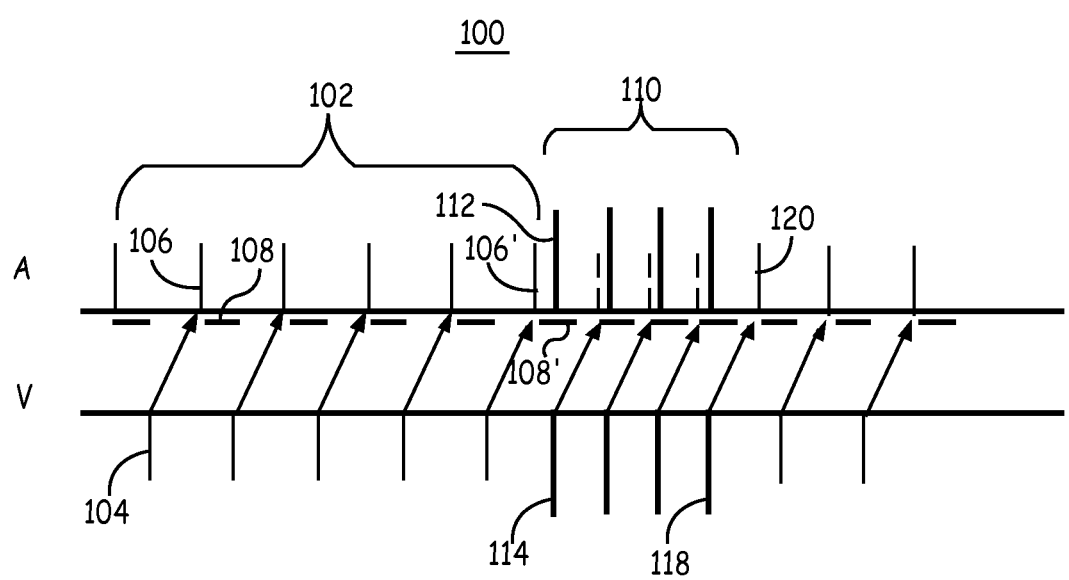
FIG. 3 is a timeline of a VT episode falsely detected as SVT.

FIG. 3 is a timeline 100 of a VT episode falsely detected as SVT. A tachycardia episode 102 is detected having 1:1 correspondence between the atrial sense events 106 (depicted as vertical lines along the upper portion of timeline 100) and the ventricular sense events 104 (depicted as vertical lines along the lower portion of timeline 100). In this case, the 1:1 tachycardia episode 102 is a ventricular tachycardia with retrograde conduction to the atrium represented by the upward diagonal arrows extending from ventricular sense events 104 to the resulting atrial sense events 106. An atrial refractory period 108 follows each atrial sense event 106.

Simultaneous dual chamber pacing 110 is initiated in an attempt to discriminate the 1:1 tachycardia 102 as ventricular or supraventricular in origin. A series of simultaneous atrial pacing pulses 112 and ventricular pacing pulses 114 are delivered at a rate faster than the detected tachycardia 102. The first atrial pacing pulse 112, however, occurs during the atrial refractory period 108' following the last atrial sensed event 106'. The total duration of the retrograde VA conduction time (not explicitly shown but generally indicated by the upward diagonal arrows) plus the atrial refractory period 108' extends after delivery of the first atrial pacing pulse 112 such that the pacing pulse 112 is unable to capture atrial tissue.

As a result, for each ventricular pacing pulse 114, retrograde conduction continues to cause atrial depolarizations represented by the dashed vertical lines during the dual chamber burst pacing. Each of these atrial depolarizations is followed by an atrial refractory period, which prevents atrial capture by the atrial pacing pulses 112.

After delivering the last ventricular pacing pulse 118, a retrograde conducted atrial depolarization is sensed as atrial sense event 120. Thus, the earliest occurring sensed event 120 following dual chamber pacing 110 is an atrial event, signifying, incorrectly, that the tachycardia is originating in the atrium. The atrial sense event 120 appears as an intrinsic event unassociated with a pacing pulse since it occurs after the dual chamber pacing 110 has stopped. The origin of the fast rhythm is thus falsely detected as supraventricular.

The situation shown in FIG. 3 generally arises when a patient has a relatively long atrial refractory period and/or a relatively long retrograde conduction time. When the patient has a relatively short atrial refractory period, the refractory period 108' may be over before the dual chamber burst pacing 110 is initiated, resulting in proper capture of the atrium during dual chamber pacing 110. However, since the atrial refractory period of the patient may be unknown, it is desirable to provide a method for delivering dual chamber pacing that results in more reliable discrimination of SVT and VT in all patients.

Figure 4A:
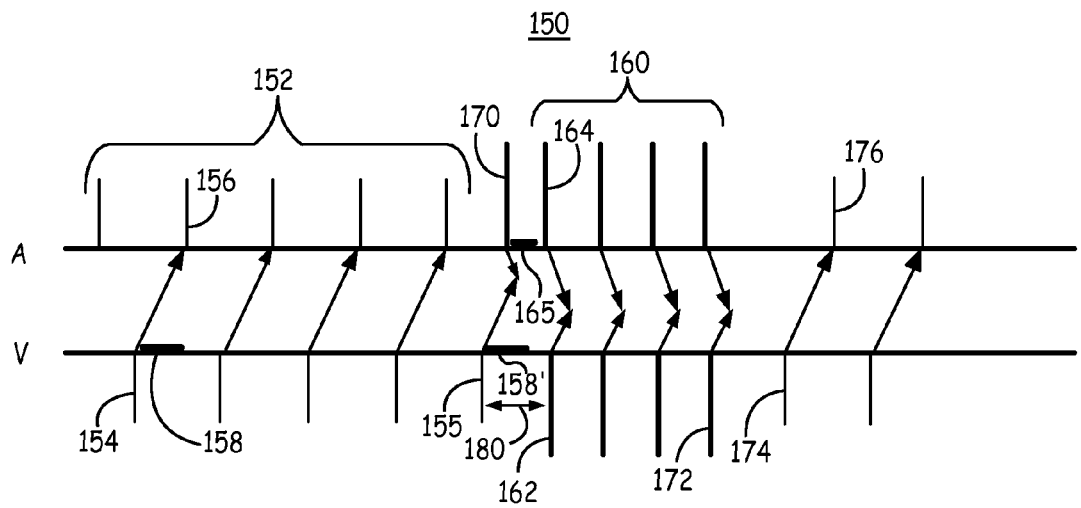
FIG. 4A is a timing diagram illustrating one method for delivering burst pacing in the atrial and ventricular regions of a patient's heart for discriminating SVT and VT.

FIG. 4A is a timing diagram 150 illustrating one method for delivering dual chamber burst pacing in the atrial and ventricular regions of a patient's heart for discriminating SVT and VT. As used herein, "dual chamber" pacing refers to pacing delivered in both atrial and ventricular regions. Dual chamber burst pacing is delivered in one or both atria and in one or both ventricles. The interval between an atrial pacing pulse and a ventricular pacing pulse during the dual chamber burst pacing is referred to as the atrial-ventricular pacing interval (AVI).

Pacing techniques described herein are provided via a controller within the IMD 10, such as the microprocessor 154 operating in conjunction with memory 156 and timing and control module 152 in FIG. 2. A controller may alternatively be implemented using one or more digital state machines. A controller providing the functionality described herein may include functionality distributed across more than one cardiac medical device component.

The timing diagram 150 of FIG. 4A includes atrial paced and sensed events shown along the top line (A) and ventricular paced and sensed events along the bottom line (V). The sensed and paced atrium can involve either or both of the patient's atria and likewise, the sensed and paced ventricle can involve either or both of the patient's ventricles.

Similar to FIG. 3, a tachycardia episode 152 is detected having 1:1 correspondence between atrial and ventricular sensed events 156 and 154 respectively. The tachycardia episode 152 is a ventricular tachycardia with retrograde conduction to the atrium (as indicated by the upward diagonal arrows) causing an atrial sense event 156 for each ventricular sense event 154. However, because the atrial event intervals and the ventricular event intervals are very similar and have 1:1 correspondence, the tachycardia episode 152 is difficult to discriminate using interval-based criteria.

Each atrial event 156 occurs after each ventricular event 154 following a retrograde, ventricular-atrial (VA) conduction time 158. The retrograde conduction time 158 may vary from patient to patient and even within a given patient when different tachycardia episodes have different ventricular sites of origin.

Dual chamber burst pacing methods described in conjunction with FIG. 4A address the situation described above in conjunction with FIG. 3 by delivering a single chamber pacing pulse 170 preceding the dual chamber pacing 160. The single chamber pacing pulse 170 is delivered in the atrium prior to the dual chamber atrial and ventricular pacing pulses 162 and 164, respectively, by a predetermined interval, also referred to herein as the "prematurity" of the single chamber pacing pulse.

Figure 4B:
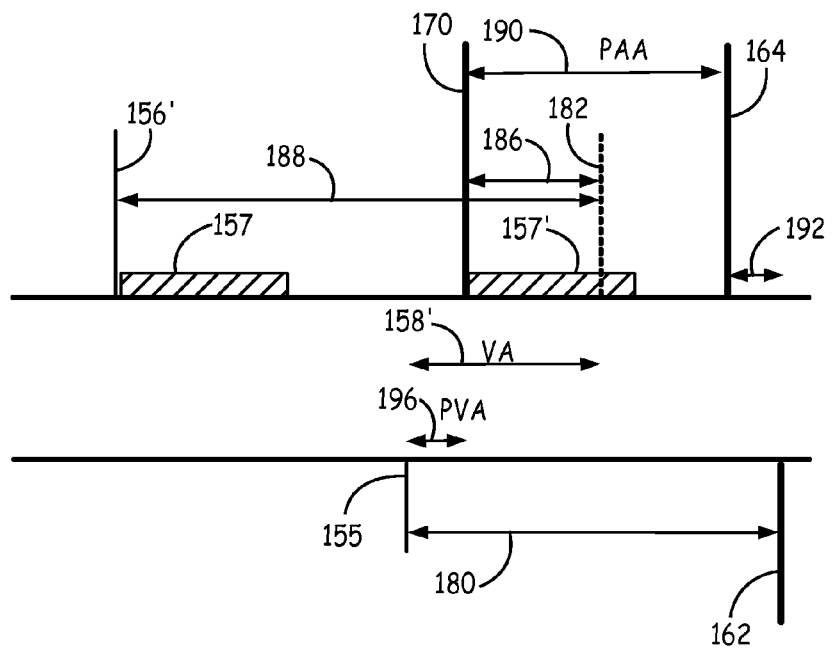
FIG. 4B is a timing diagram showing a portion of the timeline of FIG. 4A in greater detail.

FIG. 4B is a timing diagram showing a portion of the timeline of FIG. 4A in greater detail. The single chamber pacing pulse prematurity 190, also referred to as the premature paced AA (PAA) interval, may be set to a default value, for example approximately 150 ms, earlier than a scheduled dual chamber atrial pulse 164. Alternatively, a desired PAA 190 may be computed, as will be further described below in conjunction with FIG. 7.

Several requirements may be imposed on the timing of premature pacing pulse 170 to promote delivery of the premature pulse 170 at a time that will likely capture the atria and promote capture of the atria by the first dual chamber pulse 164. One requirement is that the premature pulse 170 is scheduled outside of the atrial refractory period 157 following the last atrial sense event 156'. Another requirement is that PAA 190 is longer than the atrial refractory period 157' that follows premature pulse 170 so that the first dual chamber pulse 164 falls outside refractory period 157'. The timing of the premature pulse 170 should meet these requirements while still occurring earlier than a next expected atrial sense event 182 which is intended to be blocked by premature pulse 170.

For example, as shown in FIG. 4B, the premature pulse 170 may be delivered a specified time interval 186 earlier than an expected atrial sense event 182. The expected atrial sense event 182 is the next intrinsic atrial event that would normally occur after sensed event 156' and prior to the first dual chamber atrial pacing pulse 164 if the single chamber pulse 170 were not delivered. The expected atrial sense event 182 is expected to occur at approximately the sensed atrial cycle length 188. In one embodiment, the premature atrial pacing pulse 170 is delivered at approximately 50 ms earlier than the expected atrial sense event 182. The timing of the premature pulse 170 may be based on setting an escape interval timer starting at the last atrial sensed event 156' at an interval that is equal to the sensed atrial event interval 188 less the fixed interval 186. In this way, the premature pacing pulse 170 captures the atrium during the retrograde conduction time following the last ventricular sense event 155 and thereby prevents the expected atrial sense event 182 from occurring.

In practice, the timing of the dual chamber pacing pulses 162 and 164 is generally based on the last ventricular sensed event 155 to avoid inducing ventricular tachycardia. The first ventricular pacing pulse is scheduled at a selected pacing cycle length (PCL) 180 following the last ventricular sense event 155. The first dual chamber atrial pacing pulse 164 is scheduled at an AV interval 192 relative to the first ventricular pacing pulse 162 (PCL 180 minus AV interval 192). Knowing the timing of the first dual chamber pacing pulses 162 and 164 relative to the last ventricular sense event 155, a paced ventricular atrial (PVA) interval 196 may be computed for controlling delivery of the atrial premature pulse 170 using a pacing time interval set upon the last ventricular sense event 155 and meeting the required bounds for promoting capture of both the premature pulse 170 and the first dual chamber pulse 164. Additional details regarding decision steps and computations made for controlling the delivery of premature pulse 170 will be discussed below in conjunction with FIGS. 6 and 7.

The pacing cycle length 180 is shown relative to the last ventricular sensed event 155 and the first ventricular pacing pulse 162. As such, the timing of the first atrial and ventricular pulses 164 and 162 of the dual chamber burst pacing is based on the occurrence of the last ventricular sensed event 155. This ventricular-based timing of the dual chamber burst of pacing pulses is provided to avoid inducing VT. While dual chamber pacing could conceivably be timed relative to a last atrial sensed event, the timing of the dual chamber pacing should be set to avoid inducing ventricular arrhythmias by controlling the ventricular coupling interval between the last ventricular sensed event 155 and the first ventricular pacing pulse 162.

Referring again to FIG. 4A, the premature atrial pacing pulse 170 is intended to capture (pre-excite) the atrium prior to the end of the retrograde conduction time 158' following a last ventricular sense event 155. The single-chamber atrial pacing pulse 170 will depolarize the atrium to cause an atrial refractory period 165. In this way, the single-chamber pacing pulse 170 blocks depolarization of the atrium due to the retrograde conduction of the last ventricular sense event 155. The downward diagonal arrow extending from premature pacing pulse 170 suggests the normal antegrade conduction of the atrial depolarization toward the ventricle. The upward diagonal arrow extending from the last ventricular sense event 155 indicates the retrograde conduction of the ventricular depolarization. The meeting of the two arrows schematically illustrates that the propagation of the atrial depolarization (antegrade conduction) is blocked by the ventricular refractory period as the ventricular depolarization propagates retrograde. Likewise, the propagation of the ventricular depolarization (retrograde conduction) is blocked by the atrial refractory period as the atrial depolarization propagates antegrade.

The single chamber atrial pacing pulse 170 can be thought of as a premature atrial pacing pulse as it is delivered a short interval prior to the first dual chamber pulses 162 and 164, at a selected prematurity, thus resulting in two consecutive atrial pacing pulses without an intervening ventricular pace or sense. The burst pacing interval 180 is the interval between the last ventricular sensed event 155 and the first dual chamber ventricular pulse 162 and between each of the subsequent dual chamber pacing pulses. The AVI during dual chamber pacing may be set to 0 ms for simultaneous pace pulses delivered in the atria and ventricles or to some minimal, non-zero interval (typically less than approximately 60 ms) to provide dual chamber burst pacing in the atria and ventricles.

The initial premature atrial pace 170 blocks the retrograde conduction of the final intrinsic ventricular event 155 such that subsequent atrial pacing pulses 164 are delivered outside of the atrial refractory period 165 with sufficient pulse energy to capture the atrium. These atrial pacing pulses 164 block retrograde conduction of the simultaneous ventricular pacing pulses 162. Following the final dual chamber pacing pulse 172, the first intrinsic event 174 that is sensed after dual chamber pacing 160 is a ventricular event. The fast ventricular rate reappears first after termination of the dual chamber pacing 160 signifying that the tachycardia is originating in the ventricle. The fast ventricular rate is again conducted retrograde to the atrium to cause atrial events 176 at a 1:1 correspondence with the intrinsic ventricular events 174, however, the conducted atrial events occurs after the earliest occurring sense event in the ventricle. Thus by providing a premature atrial pacing pulse prior to the dual chamber pacing burst, the earliest occurring intrinsic sensed event 174 correctly signifies the chamber of tachycardia origin.

Illustrative embodiments presented herein describe an atrial premature pacing pulse preceding a series of dual chamber pacing pulses. It is contemplated that in alternative embodiments, a premature ventricular pacing pulse may be delivered additionally or alternatively to the premature atrial pacing pulse.

Figure 5:
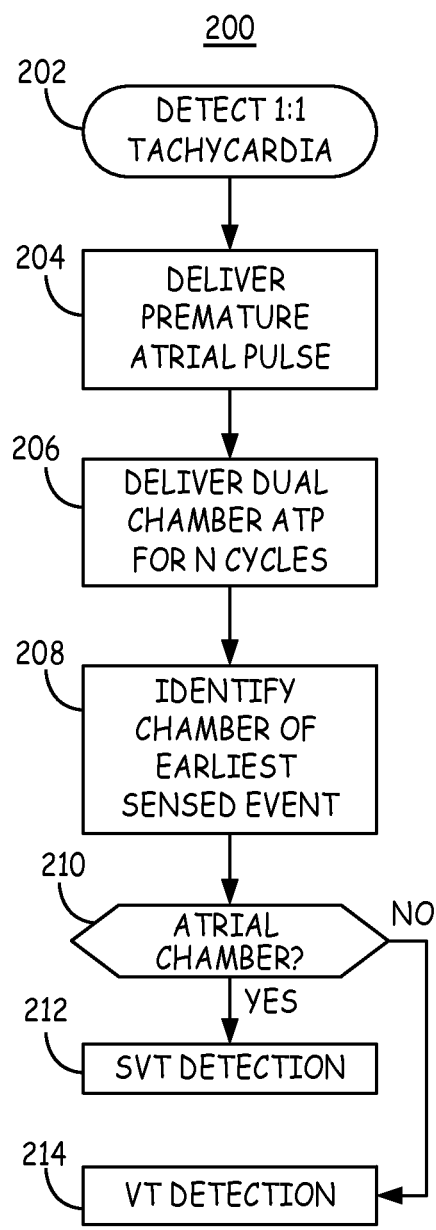
FIG. 5 is a flow chart of a method for delivering dual chamber burst pacing for use in discriminating SVT and VT.

FIG. 5 is a flow chart of a method for delivering dual chamber pacing for use in discriminating SVT and VT. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern cardiac medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 is initiated upon detecting tachycardia at block 202. Initial tachycardia detection may be made utilizing event interval, morphology or pattern based criteria or any combination thereof. At initiating block 202, detection of 1:1 correspondence in atrial and ventricular tachycardia events initiates the use of dual chamber pace discrimination methods described herein. For example, a 1:1 tachycardia may be detected when the atrial cycle lengths (P-P intervals) and ventricular cycle lengths (R-R intervals) both meet tachycardia detection criteria and are approximately equal, e.g., within approximately 30 ms of each other with one atrial event and one ventricular event occurring during each cycle. If a detected tachycardia does not have a 1:1 correspondence between atrial and ventricular sensed events, interval, morphology, and/or pattern based tachycardia discrimination methods may be used to classify the tachycardia, e.g. as SVT, VT, atrial fibrillation, dual tachycardia or sinus tachycardia. Examples of pattern-based methods for tachycardia discrimination are generally disclosed in the above-referenced '186 Olson patent.

When the atrial and ventricular cycle lengths are substantially equal, interval or pattern based rhythm classification methods may not be able to reliably discriminate VT from SVT. Dual chamber pacing is initiated to allow discrimination methods to be performed based on the heart's response to pacing. The dual chamber pacing may additionally serve to terminate the tachycardia.

As described above, in some embodiments burst pacing is initiated with a single, premature atrial pacing pulse at block 204. The single atrial pacing pulse is delivered at a predetermined interval before the first atrial pacing pulse of the dual chamber pulses. The single atrial pacing pulse is delivered at an interval defined relative to the first dual chamber atrial pacing pulse or relative to the last intrinsic, sensed ventricular event before starting the dual chamber pacing. In either case, the single atrial pacing pulse is delivered at a time interval that blocks retrograde conduction of the last sensed ventricular event.

The premature pacing pulse is delivered at a prematurity interval that is at least greater than the atrial refractory period such that the first atrial pulse of the subsequent dual chamber pulses is able to capture the atrium (falls outside the atrial refractory period associated with the premature pulse). The premature atrial pacing pulse is delivered after the last ventricular sensed event at an interval that is less than the retrograde conduction time in order to capture the atrium and thereby block retrograde conduction of the ventricular depolarization to the atrium.

At block 206, dual chamber pacing is delivered at a pacing cycle length selected to be less than the detected tachycardia cycle length. Dual chamber pacing directly follows the single chamber pacing pulse. The first dual chamber pacing pulses follow the single chamber pacing pulse by a time interval that exceeds the atrial refractory period such that the atrial pacing pulses capture the atrium. The dual chamber pacing cycle length may be set as a percentage of the tachycardia cycle length. The atrial and ventricular pacing pulses may be delivered substantially simultaneously, e.g. with a 0 ms AV interval though non-zero intervals may be used such as intervals less than approximately 60 ms. A predetermined number of dual chamber pulses may be delivered. Typically five to eight pacing cycles are delivered but methods described herein are not limited to a specific number of dual chamber pulses.

After delivering the dual chamber pacing pulses, the chamber in which the earliest occurring intrinsic event is sensed after the last pacing pulse is identified at block 208. The sensed event is an intrinsic depolarization, not an evoked response to the pacing pulses. The first chamber eliciting an intrinsic depolarization corresponds to the chamber in which the fast rate is originating. If the first chamber is an atrial chamber, i.e. the first sensed event is a P-wave as determined at block 210, the tachycardia episode is classified as SVT at block 212. If the first event is a ventricular event, i.e. an R-wave, the tachycardia episode is classified as VT at block 214.

Figure 6:
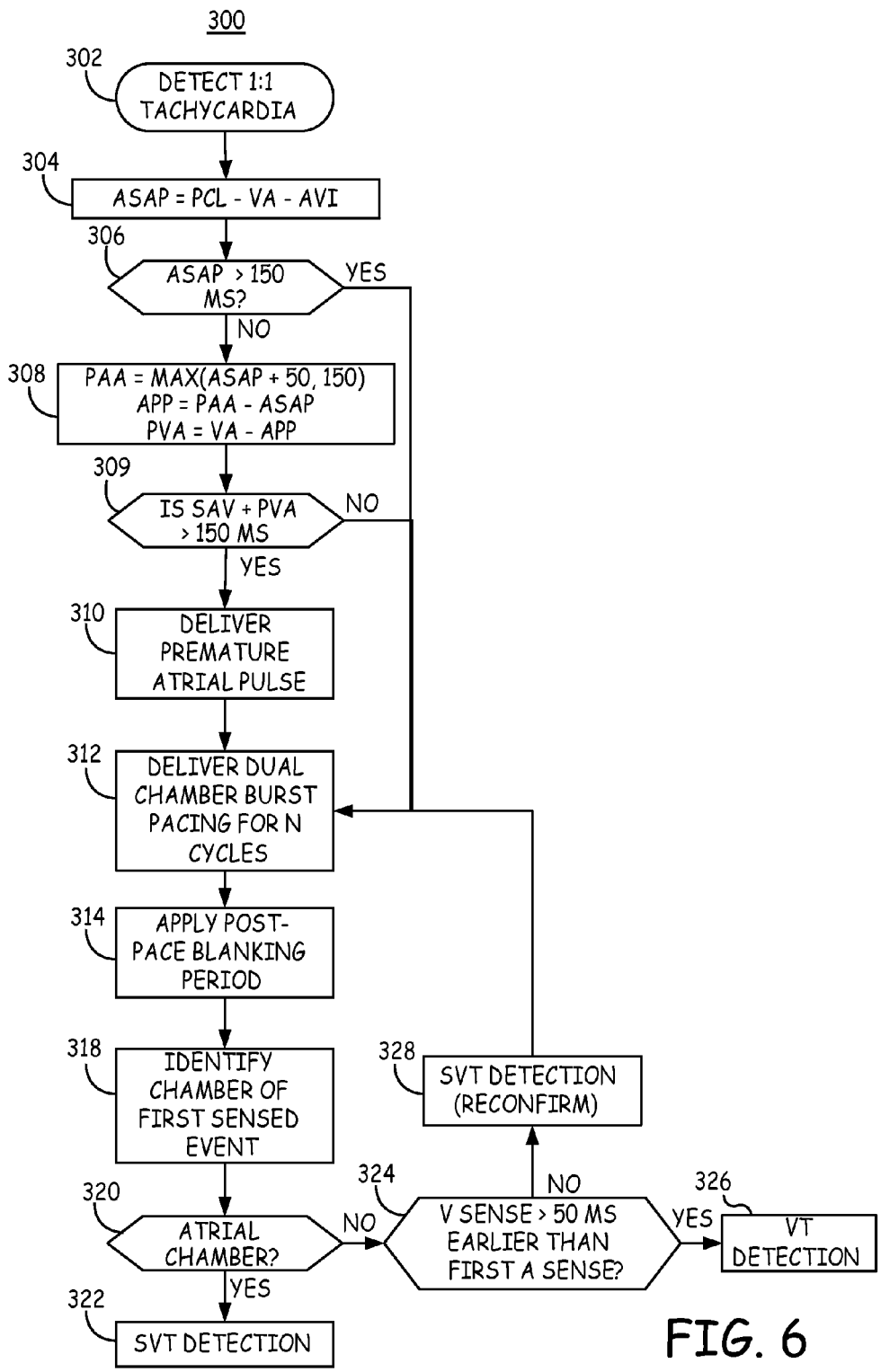
FIG. 6 is a flow chart of a method for discriminating VT and SVT according to an alternative embodiment.
Figure 7:
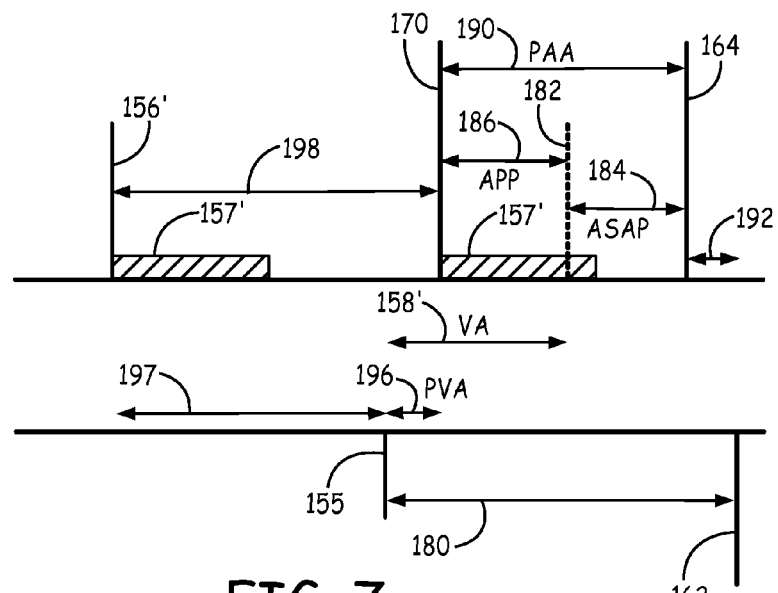
FIG. 7 is a timeline showing a premature atrial pacing pulse delivered at a paced VA interval (PVA) following the last ventricular sensed event.

FIG. 6 is a flow chart of a method 300 for discriminating VT and SVT according to an alternative embodiment. In the following description of FIG. 6, reference is also made to the timing diagram shown in FIG. 7 to more clearly illustrate computations and decisions being made in method 300. FIG. 7 corresponds to the detailed timing diagram of FIG. 4 with additional intervals indicated. Briefly, a last atrial sense event 156' and last ventricular sense event 155 are shown followed by the atrial premature pulse 170, and the first dual chamber pulses 164 (atrial) and 162 (ventricular) separated by a paced AVI 192. The premature atrial pacing pulse 170 is delivered at a PVA interval 196 following the last ventricular sense event 196.

Referring to FIG. 6, at block 302 tachycardia is detected having 1:1 correspondence in the atrial and ventricular chambers. Blocks 304 and 306 are then performed to determine whether to deliver a premature atrial pacing pulse to pre-excite the atrial chambers before initiating dual chamber burst pacing.

At block 304, a time interval between a last expected atrial sense event (if no premature pulse is delivered) and the first dual chamber atrial pacing pulse is computed. This time interval, referred to as the atrial sense-atrial pace (ASAP) interval is shown in the timing diagram of FIG. 7. The ASAP interval 184 between an expected atrial sense event 182 and the first atrial pacing pulse 164 of the dual chamber pacing is computed at block 304 as the pacing cycle length (PCL) 180 minus the VA interval 158' minus the paced AVI 192.

If the ASAP interval is greater than a predetermined limit, for example greater than 150 ms, then an atrial pacing pulse 164 following the expected atrial sense event 182 should be late enough after the expected atrial sense event 182 to occur outside atrial refractory. In this case, the first dual chamber pulse 164 is expected to be able to capture the atria. The premature atrial pacing pulse is not needed. In FIG. 6, method 300 advances directly to block 312 to deliver the dual chamber burst pacing for a desired number of pacing cycles without delivering a premature atrial pacing pulse.

If the ASAP interval 184 is less than 150 ms, there is a chance that the first atrial pacing pulse 164 of the dual chamber burst pacing will not capture the atria. A premature, single atrial pacing pulse 170 will be delivered to block the expected atrial sense event 182 that would otherwise precede the first atrial pacing pulse 164 by less than approximately 150 ms, or another predetermined limit corresponding to an estimated atrial refractory period 157'.

At block 308, computations are made to determine PVA interval 196 used to control the delivery of premature pulse 170 relative to the last ventricular sensed event 155. First a desired prematurity, i.e. PAA interval 190, between the premature atrial pacing pulse 170 and the first dual chamber atrial pacing pulse 164 is determined using the first equation in block 308. The desired PAA 190 may be computed as the ASAP interval 184 plus a predetermined fixed interval (e.g. approximately 50 ms) so that the premature atrial pulse 170 is delivered before or earlier than the expected atrial sense event 182. PAA 190 may be selected as the maximum of a selected lower limit, for example 150 ms, or the ASAP interval 184 plus a fixed interval (e.g. 50 ms) whichever is greater, as shown by the first equation in block 308.

A selected lower limit for PAA interval 190 prevents the premature atrial pacing pulse 170 from being delivered at a PAA interval 190 that is less than an expected atrial refractory period 157'. Otherwise, the first atrial pacing pulse 164 of the dual chamber burst pacing could be delivered during the physiological refractory period 157' following the premature pulse 170 and fail to capture the atria. As such, in one embodiment, the desired PAA interval 190 is 150 ms or the computed ASAP plus 50 ms, whichever is greater. PVA interval 196 can then computed as the selected pacing cycle length 180 less the programmed AVI 192 less the desired PAA 190.

Alternatively, the PVA interval 196 is computed as the difference between the sensed VA interval 158' and an interval 186 at which the atrial pacing pulse 170 will precede an expected atrial sense event 182, referred to as the atrial pace-P interval or "APP" interval 186. APP 186 is computed at block 308 according to the second equation as the difference between PAA 190 and the computed ASAP interval 184. In order to block a retrograde atrial sensed event, the premature atrial pacing pulse should be delivered earlier than the expected atrial sense event 182 but within an atrial refractory period 158' of the expected atrial sense event 182. For example, APP 186 may be set to a fixed interval of approximately 50 ms, as described in conjunction with FIG. 4B. In other embodiments, APP 186 may be variable, e.g. if the PAA interval is set to a fixed interval, e.g. 150 ms. In this case, the APP 186 is computed as the PAA interval 190 less the ASAP interval 184 as shown by the second equation in block 308. The PVA interval 196 used to control the delivery of the single atrial premature pulse 170 using an escape interval started upon the last ventricular sense event 155 is computed as the difference between the measured VA interval 158' and the APP interval 186, as shown by the third equation in block 308.

It is recognized that numerous variations in timing schemes may be conceived for controlling delivery of the atrial premature pulse. In general, the atrial premature pulse 170 should be more than one atrial refractory period 157' earlier than the first dual chamber pulse 164 (to ensure capture by the dual chamber pulse) and more than one atrial refractory period 157 later than the last atrial sense event 156' (to promote capture by the premature pulse 170), and within the VA interval 158' (to prevent the atrial sense event 182 from occurring).

At block 309, and with continued reference to FIG. 7, the timing of the premature atrial pacing pulse 170 relative to the last atrial sense event 156' is checked to ensure the premature pulse 170 is highly unlikely to fall within the physiologic refractory period 157 of the last atrial sense event 156'. The sum of the sensed AV interval 197 and the computed PVA interval 196 equals interval 198 between the last atrial sensed event 156' and the scheduled premature atrial pacing pulse 170. This interval 198 should be greater than the atrial refractory period 157 to ensure that premature pulse 170 does not fall within the atrial refractory 157 and fail to capture the atria.

As such, at block 309 of method 300, a comparison between the sum of the sensed AV interval 197 and the computed PVA interval 196 is compared to a selected interval that is equal to or greater than an estimated atrial refractory period, e.g. 150 ms. In other embodiments, the atrial refractory period may be estimated to be approximately 100 ms or anywhere between approximately 100 ms and 150 ms.

If the premature atrial pacing pulse will occur too early following the last atrial sensed event based on the determination at block 309, method 300 proceeds to block 312 and delivers dual chamber pacing without delivering a premature atrial pacing pulse. If the premature atrial pacing pulse 170 is likely to be outside of atrial refractory 157 using the computed PVA 196, according to the comparison at block 308, the premature atrial pacing pulse 170 is delivered at block 310 using the computed PVA 196 and is followed by the dual chamber burst pacing at block 312.

The dual chamber burst pacing is delivered for a desired number of cardiac cycles at a pacing cycle length that is shorter than the detected tachycardia cycle length, for example less than approximately 90% of the tachycardia cycle length. In some embodiments, the pacing cycle length is approximately 80% of the tachycardia cycle length. A selected AVI is applied during the dual chamber burst pacing.

At block 314, a tachycardia discrimination blanking period may be applied following the last dual chamber pacing pulses. In some cases, a premature contraction may be the earliest occurring intrinsic sensed event following the dual chamber pacing. As such, a blanking period may be applied to one or both of the atrial and ventricular sensed events by the ICD controller immediately following the respective atrial and ventricular pacing pulses to prevent identification of a premature contraction as the earliest occurring event signifying the origin of the tachycardia.

This tachycardia discrimination blanking period may be set to approximately equal the detected tachycardia cycle length. As such, this blanking period is generally longer than a blanking period commonly applied to sense circuitry to prevent improper sensing of pacing pulse artifact or other noise during atrial or ventricular refractory periods to avoid sensing noise or artifact as cardiac intrinsic events. The tachycardia discrimination blanking period set to an interval approximately equal to the detected tachycardia cycle length (i.e. the sensed PP or sensed RR intervals during the detected tachycardia episode prior to initiating dual chamber pacing), or to an interval slightly less than the tachycardia cycle length, will be relatively longer than the absolute blanking periods typically applied to sense circuitry to avoid sensing artifact or noise following a pacing pulse or during physiological refractory period.

The tachycardia discrimination blanking period is used to identify events that occur at a cycle length that is shorter than the originally-detected tachycardia cycle length. A sensed event occurring within the tachycardia discrimination blanking period is not relied upon alone for signifying the cardiac chamber of origin of the originally-detected tachycardia episode. The use of a tachycardia discrimination blanking interval is illustrated in FIG. 8.

Figure 8:
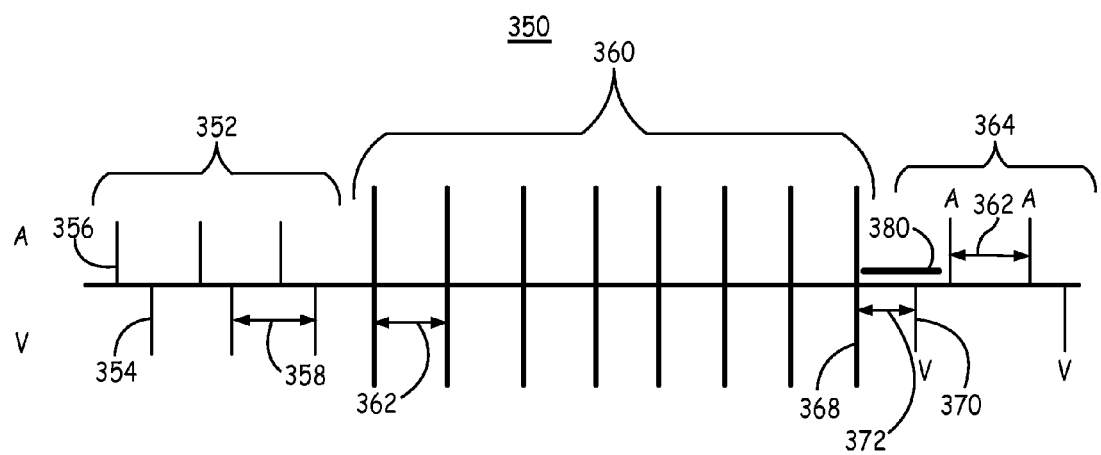
FIG. 8 is a timeline of a detected tachycardia having 1:1 correspondence between ventricular sensed events and atrial sensed events.

FIG. 8 is a timeline 350 of a detected tachycardia 352 having 1:1 correspondence between ventricular sensed events 354 and atrial sensed events 356. Dual chamber burst pacing 360 is delivered at a rate faster than the detected tachycardia rate.

Upon terminating the dual chamber burst pacing 360, the earliest occurring intrinsic sensed event 370 occurs in the ventricle. In this example, the earliest occurring event 370 is a premature ventricular contraction (PVC). The PVC 370 occurs at an interval 372 after the last ventricular pacing pulse 368 that is shorter than the detected tachycardia cycle length 358. Atrial sensed events occurring after dual chamber burst pacing 360 return at the tachycardia cycle length 362. In this example, the detected tachycardia 352 originates in the atrial chambers but may be falsely detected as VT due to the PVC 370 sensed as the earliest-occurring intrinsic event after dual chamber burst pacing 360.

To avoid this false detection of VT, a blanking interval 380 is applied directly following the dual chamber burst pacing 360. The blanking interval 380 may be set approximately equal to the detected tachycardia cycle length 362. Blanking interval 380 may be set slightly less than cycle length 362 to account for some variation in cycle length. By blanking or ignoring any events sensed at an interval shorter than the detected tachycardia cycle length, events such as premature contractions that are not associated with the originally-detected tachycardia can be ignored.

In the illustrative example of FIG. 8, a PVC 370 is shown as the earliest occurring sensed event. However, a premature atrial contraction (PAC) may similarly cause a false detection of SVT when VT is actually present and a PAC occurs as the earliest sensed event following dual chamber burst pacing 360. In various embodiments, a tachycardia discrimination blanking interval 380 may be applied to atrial sensed events, to ventricular sensed events or both atrial and ventricular events to prevent premature contractions, retrograde conducted depolarizations, or other events occurring earlier than the detected tachycardia cycle length from causing false classification of the tachycardia.

When a PVC 370 occurs following dual chamber burst pacing 360, the subsequently sensed events commonly exhibit a pattern of VAAV 364. In other words, a sensed event 370 in the ventricles is followed by two atrial sensed events and then another ventricular sensed event. This post-pace VAAV pattern 364 may also be used to discriminate between SVT and VT. When a VAAV pattern 364 occurs following the dual chamber pacing, the first V event is likely a PVC followed by the atrial events corresponding to an atrial tachycardia, particularly when the earliest occurring V sense event occurs during a tachycardia discrimination blanking interval. This VAAV pattern and other pattern analysis useful in paced tachycardia discrimination methods will be further discussed below.

Returning to FIG. 6, the chamber in which the earliest intrinsic, sensed event occurs is identified at block 318. When the blanking interval is applied at block 314, this earliest occurring event will be outside the tachycardia discrimination blanking interval, i.e. a non-blanked event. In some embodiments, any earlier events, falling within the tachycardia discrimination blanking period, are ignored for the purposes of discriminating the tachycardia.

Alternatively, as will be described further below, blanking interval events are used in discrimination algorithms to evaluate post-pace sensed event patterns. In either case, however, the blanking period is used to distinguish between intrinsic, sensed events that correspond to the rate and chamber of origin of the detected tachycardia and sensed events that do not correspond to either the rate or the chamber of origin of the detected tachycardia. In other words, an earliest occurring event within the tachycardia discrimination blanking interval cannot be used alone in discriminating the tachycardia. At least one additional event outside the blanking interval is required for reliably discriminating the tachycardia.

If the earliest occurring non-blanked event is in the atrial chamber, as determined at block 320, the tachycardia is detected as SVT at block 322. The ICD may deliver an atrial ATP therapy according to a menu of therapies. SVT detection will prevent ventricular ATP therapies from being delivered unnecessarily.

If the earliest occurring non-blanked event is in the ventricular chamber (a negative result at block 320), the timing of the earliest ventricular sense event relative to the next atrial sense event may be evaluated at block 324 before detecting the tachycardia as VT at block 326. For example, if the ventricular sense event is at least some predetermined interval earlier than the first atrial sense event (non-blanked), e.g. approximately 50 ms earlier, the tachycardia is detected as VT (block 326). An ATP therapy may be delivered to treat the VT according to programmed therapies.

If the earliest occurring ventricular sense event is less than 50 ms earlier than the earliest occurring atrial sense event, the tachycardia is likely to be SVT, but the two events may be too close together to reliably discriminate between VT and SVT. As such, SVT may be preliminarily detected at block 328, preventing or delaying any scheduled VT therapy, and the dual chamber pace discrimination method may be repeated by returning to block 312 to confirm the SVT detection.

It is recognized that repeating the dual chamber pace discrimination method by returning to block 312 to confirm a preliminary detection may include delivering a premature atrial pacing pulse if a PVA interval can be utilized that meets the timing requirements of the premature pacing pulse relative to the last atrial sensed event and the first dual chamber atrial pacing pulse as described previously. In some embodiments, if a premature single chamber pacing pulse was included in the initial attempt at dual chamber pace discrimination, the premature signal chamber pacing pulse may be excluded on a repeated attempt to allow comparisons of the post-pacing response with and without the premature pulse. Likewise, if the premature pulse was not included during the initial burst pacing, a premature pacing pulse may be added in repeated attempts as long as a premature pacing interval does not result in the pacing pulse being delivery during an expected refractory period of the last atrial sense event.

If a premature single chamber pacing pulse is delivered during repeated pace discrimination attempts, it may be delivered at a different prematurity interval than an initial premature pulse interval. Different prematurity intervals may be provided by varying the prematurity by a fixed interval from a computed PVA, e.g. between approximately 10 to 50 ms increments or decrements. Different prematurity intervals may alternatively be provided by varying the fixed interval added to the ASAP interval in the first equation of block 308 used for computing a desired prematurity. The PVA may be varied as long as the requirement at block 309 continues to be met.

Figure 9:
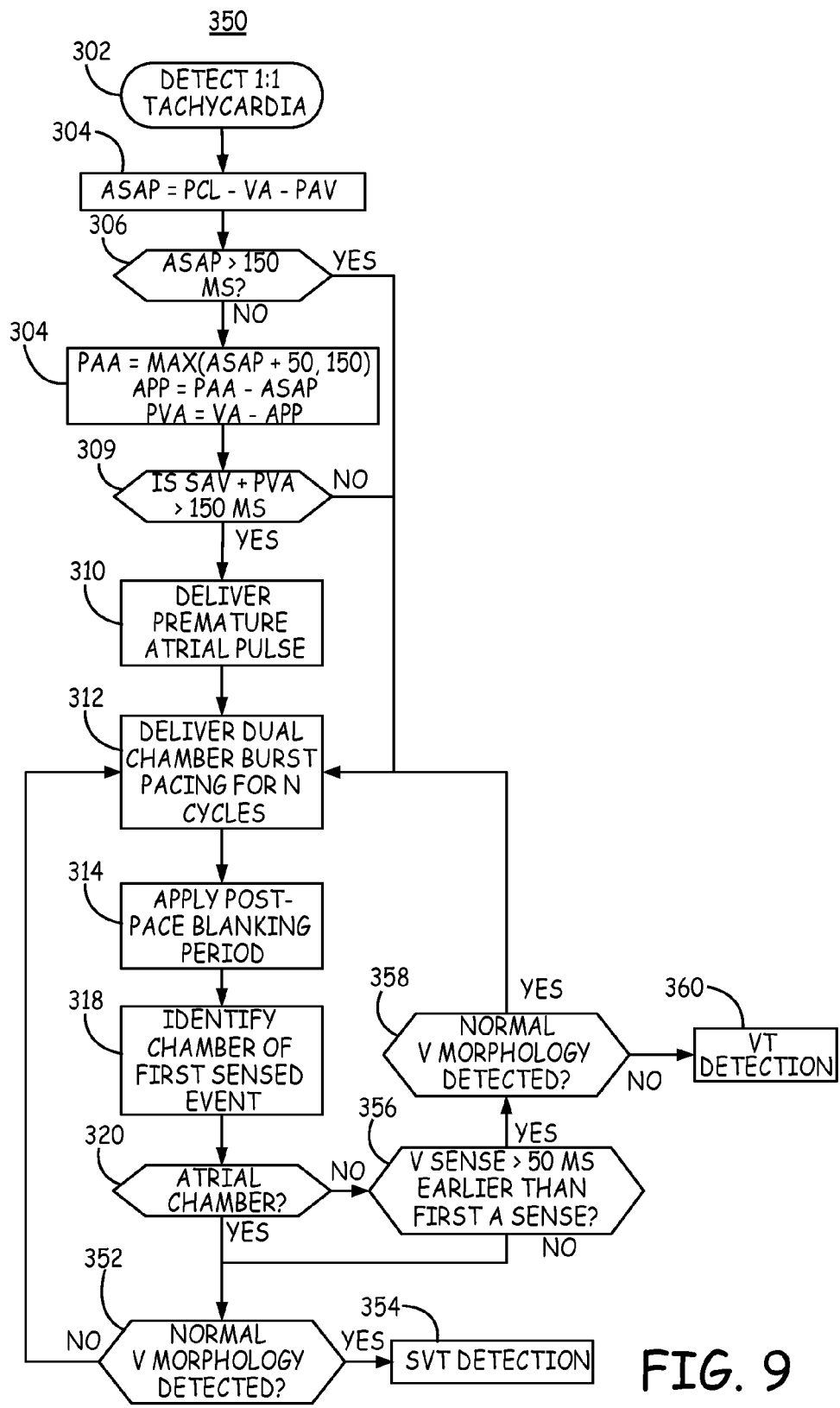
FIG. 9 is a flow chart of an alternative method for paced tachycardia discrimination.

FIG. 9 is a flow chart 350 of an alternative method for paced tachycardia discrimination. In FIG. 9, identically numbered blocks correspond to those shown in FIG. 6. In the method shown in FIG. 9, after identifying the chamber in which the earliest non-blanked sensed event occurs, a morphology analysis may be performed for discriminating VT and SVT.

If the earliest occurring event is an atrial event (block 320) indicating SVT, the ventricular signal may be analyzed to support the SVT detection. If the morphology substantially matches a known normal morphology corresponding to a ventricular depolarization conducted from the atrial chambers, as determined at block 352, SVT is detected at block 354. A variety of morphology analysis methods may be used which typically include comparisons between the unknown ventricular signal and a known template. Reference is made, for example, to the above-incorporated '316 Gillberg patent.

If the ventricular signal morphology does not substantially match a known normal morphology corresponding to a conducted ventricular event, the dual chamber pacing discrimination method may be repeated by returning to block 312 (which may include delivering a premature atrial pacing pulse as described above).

If the earliest occurring event is a ventricular event and is sensed less than 50 ms earlier than the earliest atrial event (block 356), the rhythm is most likely SVT. Morphology analysis is performed at block 352 to confirm a normal ventricular signal morphology before making the SVT detection at block 354. If the earliest occurring event is a ventricular event that is more than 50 ms earlier than the earliest atrial event (block 356), the tachycardia is most likely ventricular in origin. However, morphology analysis may be performed at block 358 to support this conclusion. If the ventricular signal morphology is determined to match a normally-conducted depolarization signal morphology, the results of the morphology analysis and the earliest occurring event being ventricular and greater than 50 ms earlier than the next atrial event provide inconsistent or conflicting results. The paced discrimination method may be repeated by returning to block 312.

A ventricular signal morphology that does not match a known morphology for a normally conducted ventricular depolarization corroborates the evidence for VT based on the earliest occurring event being a ventricular event greater than 50 ms earlier than the next atrial event. VT is detected at block 360. Morphology analysis may thus be incorporated into the paced discrimination methods to confirm an event-based discrimination or to cause pace discrimination methods to be repeated until non-conflicting results are obtained, the tachycardia is terminated or a maximum number of attempts or other time limit is reached. Some maximum limit may be applied to the number of dual chamber pacing episodes that are attempted to discriminate the tachycardia before a therapy delivery decision is made.

Figure 10:
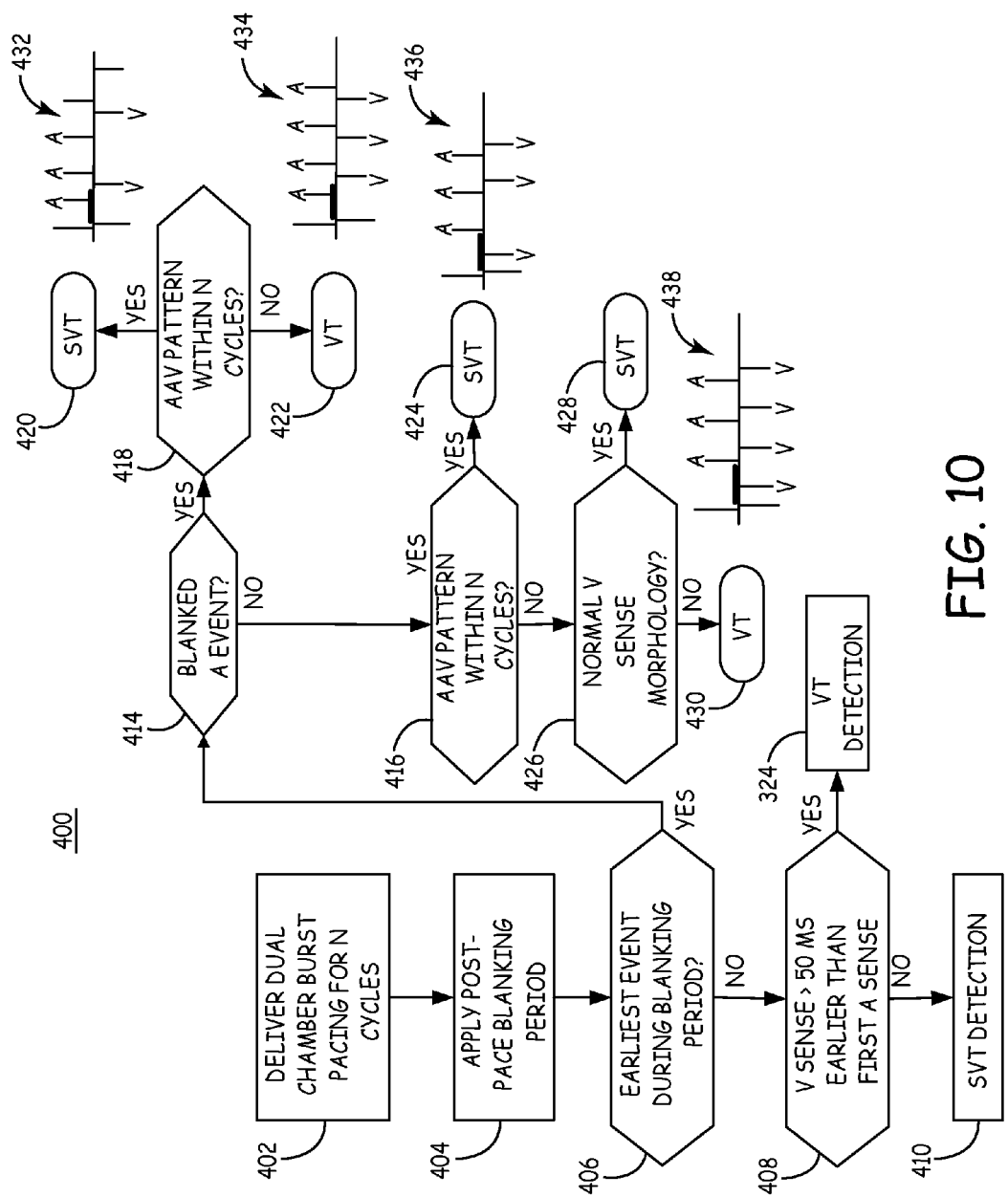
FIG. 10 is a flow chart of a method for discriminating tachycardia using analysis of the post-paced event pattern.

FIG. 10 is a flow chart 400 of a method for discriminating tachycardia using additional analysis of the post-paced event pattern. At block 402, dual chamber burst pacing is delivered for a desired number of cardiac cycles (N). The delivery of dual chamber burst pacing may include a premature atrial pulse as described above. At block 404, a post-pace, tachycardia discrimination blanking period is applied to separate events highly likely to be indicative of the chamber of tachycardia origin and events that are highly unlikely to be indicative of the originally-detected tachycardia. An event occurring within the tachycardia discrimination blanking period is occurring at a cycle length that is shorter than the originally detected tachycardia cycle length as described previously.

At block 406, a determination is made whether the earliest occurring intrinsic event after the dual chamber burst pacing is sensed during the tachycardia discrimination blanking interval. If the earliest event is a non-blanked ventricular sense event that is a predetermined minimum interval earlier than the earliest atrial sense event (block 408), the tachycardia is detected as VT. If the earliest event is a non-blanked ventricular sensed event less than the predetermined minimum interval (block 408), SVT is detected at block 410. As described above, additional analysis, such as morphology analysis or repeated dual chamber burst pacing may be delivered to allow confirmation of the SVT detection at block 410.

When the earliest event occurs during the tachycardia discrimination blanking interval, as determined at block 406, additional analysis of the subsequent sensed event pattern is performed to discriminate the tachycardia. If the earliest occurring event is a blanked atrial event as determined at block 414, an analysis of the next N cardiac cycles is performed at block 418.

If an AAV pattern is present within the next N cycles, for example within the next five cardiac cycles, which may or may not include the cycle beginning with the blanked atrial event, SVT is detected at block 420. This situation is illustrated in the inset timeline 432. A blanked atrial event is likely to be a premature atrial contraction which is conducted to the ventricle causing the earliest occurring event outside the blanking interval to be a ventricular event. A tachycardia detection based on the first non-blanked event alone, therefore, would potentially classify the tachycardia as VT. However, the subsequent AAV pattern is evidence of SVT and the pattern analysis triggered by the blanked atrial event allows a correct SVT detection to be made at block 420.

If no AAV pattern is present within the next N intervals (block 418), the earliest ventricular event outside the blanking interval correctly indicates VT as detected at block 422. The absence of the AAV pattern as depicted in the inset timeline 434 indicates that the fast ventricular rate appearing first after the dual chamber pacing and the tachycardia discrimination blanking interval is indeed associated with VT. The blanked atrial event was likely to be a premature atrial contraction and not indicative of the chamber of origin of the originally-detected tachycardia.

When the blanked event is a ventricular event (negative result at block 414), the next N cycles may also be analyzed to detect the presence of the AAV pattern indicative of SVT. If present, SVT is detected at block 424. In this situation, illustrated by the inset timeline 436, the blanked ventricular event is likely to be a premature ventricular contraction followed by the reappearance of a fast atrial rate.

If the AAV pattern is not present following a blanked ventricular event, morphology analysis is performed at block 426. This situation is depicted in the inset timeline 438. In this case, the 1:1 correspondence of atrial and ventricular events may correspond to an SVT with the blanked ventricular event being a premature ventricular contraction followed by a retrograde-conducted atrial event and this VAVA pattern continues after the blanking interval. Alternatively, the blanked ventricular event may be a premature ventricular contraction followed by the reappearance of a fast atrial rate conducted 1:1 to the ventricles. As such, the event analysis alone is not sufficient to discriminate the tachycardia.

Morphology analysis of ventricular sense events is performed at block 426 on one or more non-blanked ventricular sense events. If the ventricular signal morphology substantially matches a known morphology corresponding to a normally conducted ventricular depolarization, SVT is detected at block 428. If the ventricular signal morphology is determined to not be associated with a normally conducted ventricular depolarization, i.e., likely to originate in the ventricles, VT is detected at block 430. Alternatively or additionally, pace discrimination attempts may be repeated to confirm a result.

In summary, if an earliest occurring event following dual chamber pacing falls within a tachycardia discrimination blanking interval, which is set based on the detected tachycardia cycle length, additional event pattern analysis and/or morphology analysis may be invoked to evaluate subsequent, non-blanked events, to classify the tachycardia.

Figure 11:
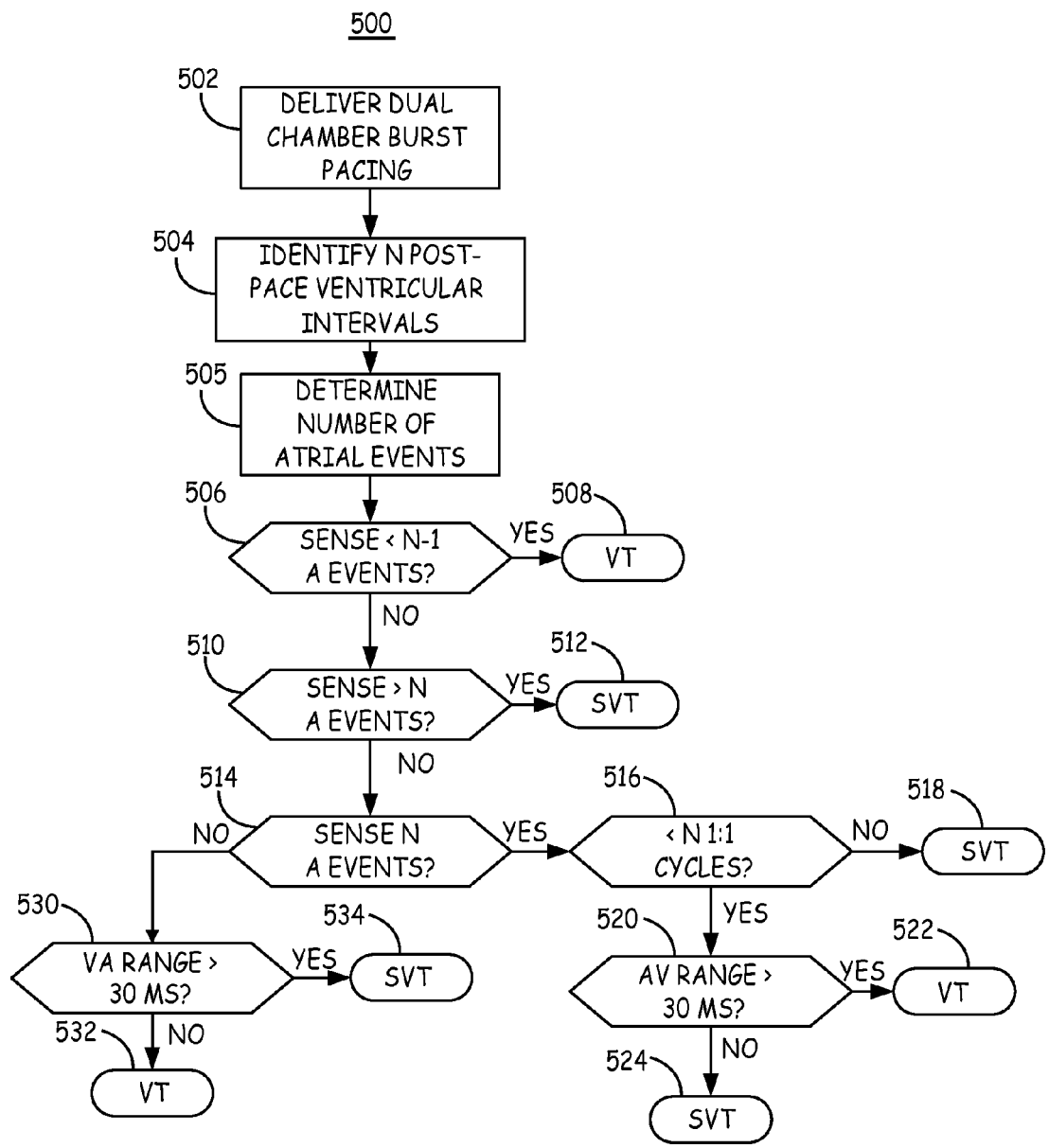
FIG. 11 is a flow chart of an alternative method for dual chamber pacing discrimination of tachycardia.

FIG. 11 is a flow chart 500 of an alternative method for dual chamber pacing discrimination of tachycardia. In method 500, dual chamber burst pacing is delivered at block 502 for a desired number of cardiac cycles as described previously without applying a tachycardia discrimination blanking interval. A premature atrial pacing pulse may or may not be applied. At block 504, a desired number of post-pace ventricular cycles (N) are identified. The N ventricular cycles are identified by identifying the earliest-occurring ventricular sense event after the last dual chamber pacing pulse and the subsequent N+1 ventricular sense events.

At block 505, the number of atrial sense events occurring during the N ventricular cycles is determined. The number of atrial sensed events is then compared to the number of ventricular cycles N in subsequent decision blocks 506, 510 and 514. When the number of sensed atrial events is less than N−1, VT is detected at block 508. The greater number of ventricular events is indicative of a fast rate originating in the ventricular chambers. Only one ventricular cycle more than the number of atrial events may be associated with a PVC; and is thus would not be sufficient evidence to detect VT. Accordingly, the requirement to detect VT at block 508 is that there is less than N−1 atrial events during the N ventricular cycles as determined at block 506.

If there are more atrial events than ventricular cycles, i.e. more than N atrial sense events as determined at block 510, SVT is detected at block 512. The greater number of atrial events during N ventricular cycles indicates a fast atrial rate and is evidence of tachycardia originating in the supraventricular region of the heart.

If the number of atrial sense events is exactly equal to N−1, (a negative result at each of decision blocks 506, 508 and 514), the single ventricular event not associated with an atrial sense event may be a premature ventricular contraction. On the other hand, one more ventricular event than atrial events may be caused by a VT with 1:1 retrograde conduction, i.e. every atrial sensed event is conducted retrograde from the ventricles. Additional analysis is need to discriminate between these two conditions.

In one embodiment, the VA interval range is determined at block 530 and compared to a threshold. The VA interval range can be determined by computing the VA interval for each of the N cycles. The maximum VA interval and the minimum VA interval for the N cycles are then identified. The VA interval range is the difference between the maximum and minimum VA intervals. It is recognized that other computations may be made to determine a metric of the range or variability of VA intervals occurring during the N ventricular cycles. For example, in some embodiments, only a maximum VA interval may be evaluated.

If the VA interval range is relatively small, for example less than approximately 30 ms, VT is detected at block 532. If the VA interval range is large, e.g., exceeds a threshold of 30 ms or another selected threshold value, SVT is detected at block 534. When the VA interval range is relatively small, VT is indicated because atrial events occurring at a regular interval following ventricular events likely represents retrograde conduction of the fast ventricular rhythm to the atria.

A relatively large VA interval range is not typical during VT and indicates the atrial and ventricular events are not highly associated, e.g. at least one ventricular ectopic event may be present. As such a relatively large VA interval range, as defined by the selected threshold value, is indicative of SVT.

When the number of atrial sense events equals N, as determined at block 514, the degree of 1:1 correspondence between atrial and ventricular events during the N cycles is analyzed at block 516. If 1:1 correspondence between each ventricular sense event and each atrial event does not exist for all N ventricular cycles, an AAV pattern is present indicative of SVT. SVT is detected at block 518. Examples of AAV interval patterns that correspond to SVT are shown in the inset timelines 432 and 436 shown in FIG. 10.

If each of the N ventricular cycles is associated with one atrial sense event at block 516, i.e. all N cycles have 1:1 correspondence between atrial and ventricular sense events, additional analysis of the timing relationship between atrial and ventricular sense events is required to discriminate between SVT and VT. In one embodiment, the AV interval range is determined and compared to a threshold at block 520. The AV interval range may be determined by measuring the AV interval for each of the N ventricular cycles and identifying the maximum and minimum AV intervals. The AV interval range is the difference between the maximum and minimum. It is recognized that other methods may be used for computing a metric of the range or variation of AV intervals during the N ventricular cycles.

If the AV interval range is greater than a threshold, such as approximately 30 ms, as determined at block 520, VT is detected at block 522. If the AV interval range is less than the threshold, SVT is detected at block 524. Analogous to the previously described analysis of the VA interval, if the AV interval is regular, i.e. a small AV interval range, the ventricular events are likely being conducted regularly from the atria. As such, a relatively small AV interval range as defined by the selected threshold is evidence of the tachycardia originating in the supraventricular region and being conducted to the ventricles.

If the AV interval range is large, at least one atrial sense event is unlikely to be associated with a subsequent ventricular sense event, even though they occur with 1:1 correspondence. This suggests that the fast ventricular rate is not originating in the atria. For example, the first atrial sense event may be a premature atrial contraction following pacing and subsequent atrial sense event may be conducted in 1:1 correspondence from the ventricles. In the case of a large AV interval range, VT is detected at block 522.

Method 500 is described based on identifying N ventricular cycles. It is contemplated, however, that a similar analysis could be performed by identifying N atrial cycles and subsequently evaluating the relationship of ventricular sense events, in timing and in pattern, to the atrial events.

In summary, instead of identifying only the earliest occurring sensed intrinsic event following the dual chamber pacing, the method shown in flow chart 500 includes analysis of a group of post-pace cardiac cycles to determine pattern and timing relationships between atrial and ventricular sensed events that can be used to reliably discriminate VT and SVT. This analysis generally includes identifying the degree of 1:1 correspondence or lack thereof, and identifying the variability of the time intervals between atrial and ventricular sensed events. While a particular algorithm is shown in FIG. 11, it is recognized that numerous variations of methods for analyzing a group of post-pace cardiac cycles may be conceived for discriminating the possible patterns and timing relationships of atrial and ventricular sense events and correlating those patterns and timing relationships to either VT or SVT.

Thus, a cardiac medical device and associated method have been presented in the foregoing description with reference to specific embodiments. It is appreciated that various modifications to the referenced embodiments may be made without departing from the scope of the invention as set forth in the following claims.

The invention claimed is:

1. A cardiac medical device for delivering anti-tachycardia pacing, comprising:
   a plurality of electrodes implantable within a patient for sensing cardiac signals and delivering cardiac pacing pulses;
   a therapy delivery module coupled to the plurality of electrodes for delivering pacing pulses to the patient's heart via the plurality of electrodes; and
   a controller coupled to the therapy delivery module and adapted to be electrically connected to the plurality of electrodes, the controller configured to:
     detect a tachycardia episode from the cardiac signals,
     control the therapy delivery module to deliver, via the plurality of electrodes, a plurality of dual chamber pacing pulses in response to detecting the tachycardia episode;
     in response to sensing an earliest occurring intrinsic event in a first cardiac chamber, identify a plurality of cardiac cycles in the first cardiac chamber comprising the earliest occurring sensed intrinsic event and a predetermined number of subsequent sensed intrinsic events occurring in the first cardiac chamber subsequent to the dual chamber pacing pulses;
     determine how many sensed intrinsic events occur in a second cardiac chamber during the plurality of cardiac cycles in the first chamber as a number of second chamber events; and
     classify the detected tachycardia episode as originating in the second cardiac chamber in response to the earliest occurring intrinsic event in the first cardiac chamber and the determined number of second chamber events being greater than the predetermined number of subsequent sensed intrinsic events occurring in the first cardiac chamber during the identified plurality of cardiac cycles in the first chamber.

2. The device of claim 1 wherein the controller is further configured to:
   determine if the number of second chamber events equals the plurality of cardiac cycles in the first cardiac chamber;
   determine if the sensed second chamber events occur in 1:1 correspondence with the plurality of cardiac cycles in response to determining an equal number of second chamber events equals the plurality of cardiac cycles; and
   classify the detected tachycardia episode in response to determining the 1:1 correspondence.

3. The device of claim 2 wherein the controller is further configured to determine an interval between an event occurring in the second chamber and an event occurring in the first chamber in response to not determining 1:1 correspondence between the second chamber events and the plurality of cardiac cycles; and
   classify the detected tachycardia episode in response to the interval.

4. The device of claim 3 wherein the controller is further configured to determine a plurality of intervals between events occurring in the second chamber and events occurring in the first chamber;
   compute a range of the plurality of intervals,
   compare the range to a threshold, and classify the detected tachycardia episode in response to the threshold comparison.

5. The device of claim 1 wherein the controller is further configured to determine an interval between an event occurring in the first chamber and a subsequent event occurring in the second chamber; and
   classify the detected tachycardia episode in response to the interval.

6. The device of claim 5 wherein the controller is further configured to determine a plurality of intervals between an event occurring in the first chamber and a subsequent event occurring in the second chamber in response to determining the number of second chamber events being one less than the plurality of cardiac cycles,
   compute a range of the plurality of intervals;
   compare the range to a threshold, and
   classify the detected tachycardia episode in response to the threshold comparison.

7. The device of claim 1 wherein the controller is further configured to:
   classify the tachycardia episode as ventricular tachycardia in response to the number of second chamber events being at least two less than the plurality of cardiac cycles occurring in the first cardiac chamber,
   determine a range of intervals between events in the first cardiac chamber and events the second chamber events in response to the number of second chamber events being exactly equal to one less than the plurality of cardiac cycles occurring in the first cardiac chamber, and
   classify the detected tachycardia episode in response to the range of intervals.

8. A cardiac medical device for delivering anti-tachycardia pacing, comprising:
   a plurality of electrodes implantable within a patient for sensing cardiac signals and delivering cardiac pacing pulses;
   a therapy delivery module coupled to the plurality of electrodes for delivering pacing pulses to the patient's heart via the plurality of electrodes; and
   a controller coupled to the therapy delivery module and adapted to be electrically connected to the plurality of electrodes, the controller configured to:
     detect a tachycardia episode from the cardiac signals,
     control the therapy delivery module to deliver, via the plurality of electrodes, a plurality of dual chamber pacing pulses in response to detecting the tachycardia episode; and
     analyze a group of cardiac cycles after the dual chamber pacing to classify the detected tachycardia episode as being one of ventricular tachycardia and supraventricular tachycardia.

* * * * *